United States Patent
McGrath

(10) Patent No.: US 7,217,690 B2
(45) Date of Patent: May 15, 2007

(54) COMPOSITIONS OF SUNFLOWER TRYPSIN INHIBITORS

(75) Inventor: Kevin P. McGrath, Alpharetta, GA (US)

(73) Assignee: Kimberly-Clark Worldwide, Inc., Neenah, WI (US)

(*) Notice: Subject to any disclaimer, the term of this patent is extended or adjusted under 35 U.S.C. 154(b) by 472 days.

(21) Appl. No.: 10/680,557

(22) Filed: Oct. 7, 2003

(65) Prior Publication Data
US 2005/0075278 A1   Apr. 7, 2005

(51) Int. Cl.
| | |
|---|---|
| A61K 38/12 | (2006.01) |
| A61K 38/00 | (2006.01) |
| A61K 38/02 | (2006.01) |
| A61K 38/10 | (2006.01) |
| A61K 38/08 | (2006.01) |
| C07K 2/00 | (2006.01) |
| C07K 5/12 | (2006.01) |
| C07K 7/64 | (2006.01) |
| C07K 7/08 | (2006.01) |
| C07K 7/04 | (2006.01) |

(52) U.S. Cl. .................. 514/9; 514/2; 514/10; 514/11; 514/14; 514/15; 530/300; 530/317; 530/321; 530/327; 530/328

(58) Field of Classification Search .............. None
See application file for complete search history.

(56) References Cited

U.S. PATENT DOCUMENTS

| | | | |
|---|---|---|---|
| 4,906,457 A | 3/1990 | Ryan | |
| 5,807,555 A | 9/1998 | Bonte et al. | |
| 6,096,327 A | 8/2000 | Lezdey et al. | |
| 6,294,181 B1 | 9/2001 | Lezdey | |
| 6,344,189 B1 | 2/2002 | Bunn et al. | |
| 6,586,403 B1 * | 7/2003 | Mathison et al. | 514/18 |
| 2003/0113388 A1 | 6/2003 | Phan | |
| 2003/0143186 A1 | 7/2003 | Underiner et al. | |
| 2005/0058672 A1 | 3/2005 | Gupta | |

FOREIGN PATENT DOCUMENTS

| | | |
|---|---|---|
| CA | 2019974 | 6/1991 |
| GB | 2355193 | 4/2001 |
| JP | 3-181422 | 8/1991 |
| JP | 6-080554 | 3/1994 |
| JP | 11-193207 | 7/1999 |
| WO | WO-99/45974 A1 | 9/1999 |
| WO | WO-99/49887 A1 | 10/1999 |
| WO | WO 200031139 A1 * | 6/2000 |
| WO | WO-01/74320 A2 | 10/2001 |
| WO | WO-03/013458 A1 | 2/2003 |
| WO | WO-03/041744 A2 | 5/2003 |
| WO | WO-2004/045634 A1 | 6/2004 |
| WO | WO-2005/051635 A1 | 6/2005 |

OTHER PUBLICATIONS

J. Rudinger. In: Peptide Hormones, JA Parsons, Ed. (1976) 1-7.*
W.S. Messer, "Vasopressin and Oxytocin", web document updated Apr. 3, 2000; <http://www.neurosci.pharm.utoledo.edu/MBC3320/vasopressin.htm>; 5 pages.*
D.E. Smilek, et al. Proc. Natl. Acad. Sci. USA (1991) 88, pp. 9633-9637.*
Sunflower seeds. George Mateljan Foundation. Web document. <http://www.whfoods.com/genpage.php?tname=foodspice&dbid=57>, Accessed Jun. 28, 2006,. published online Aug. 25, 2002. 4 pages.*
S. Luckett et al. J. Mol. Biol. (1999) 290, pp. 525-533.*
Brauer, A. B., et al., "The (1)H-NMR solution structure of the antitryptic core peptide of Bowman-Birk inhibitor proteins: a minimal canonical loop.", *J Biomol Struct Dyn.*, 20(1), (Aug. 2002), 59-70.
Korsinczky, M. L., et al., "Solution structures by 1H NMR of the novel cyclic trypsin inhibitor SFTI-1 from sunflower seeds and an acyclic permutant.", *J Mol Biol.*, 311(3), (Aug. 2001), 579-591.
Long, Y. Q., et al., "Synthesis and evaluation of the sunflower derived trypsin inhibitor as a potent inhibitor of the type II transmembrane serine protease, matriptase.", *Bioorg Med Chem Lett.*, 11(18), Sep. 2001, 2515-2519.
Marx, U. C., et al., "Enzymatic cyclization of a potent bowman-birk protease inhibitor, sunflower trypsin inhibitor-1, and solution structure of an acyclic precursor peptide.", *J Biol Chem.*, 278(24), (Jun. 2003), 21782-21789.
McBride, J. D., et al., "Peptide mimics of the Bowman-Birk inhibitor reactive site loop.", *Biopolymers.*, 66(2), (2002), 79-92.
Zablotna, E., "Chemical synthesis and kinetic study of the smallest naturally occurring trypsin inhibitor SFTI-1 isolated from sunflower seeds and its analogues.", *Biochem Biophys Res Commun.*, 292(4), (Apr. 2002), 855-859.
Mulvenna, J. P., et al., "Discovery, structural determination, and putative processing of the precursor protein that produces the cyclic trypsin inhibitor sunflower trypsin inhibitor 1", *J Biol Chem.*, 280(37), (Sep. 16, 2005),32245-53.
Atherton, D. J., "A Review of the Pathophysiology, Prevention and Treatment of Irritant Diaper Dermatitis", *Current Medical Research and Opinions*, 20(5), (2004), 645-649.
Descours, A., et al., "A New Family of β-Hairpin Mimetics Based on a Trypsin Inhibitor from Sunflower Seeds", *ChemBioChem*, 3(4), (2002), 318-323.
Fiorillo, L., "Therapy of Pediatric Genital Diseases", *Dermatogic Therapy*, 17, (2004), 117-128.
Flagothier, C. , et al., "Comment J'Explore les Dermites des Langes [How I Explore . . . Diaper Dermatitis]" (w/ English Abstract), *Revue Medicale de Liege*, 59(2), (2004), 106-109.
Korsinczky, M. L., et al., "Sunflower Trypsin Inhibitor-1", *Current Protein and Peptide Science*, 5(5), (2004), 351-364.
Odio, M. et al., "Diaper Dermatitis and Advances in Diaper Technology", *Current Opinions in Pediatrics*, 12(4), (2000), 342-346.
Prasad, H. R., "Diapers and Skin Care: Merits and Demerits", *Indian Journal of Pediatrics*, 71(10), (2004),907-908.

* cited by examiner

Primary Examiner—Cecilia J. Tsang
Assistant Examiner—Andrew D. Kosar
(74) Attorney, Agent, or Firm—Schwegman, Lundberg, Woessner, & Kluth, P.A.

(57) ABSTRACT

The present invention provides methods of using small cyclic peptides that can inhibit or prevent skin irritation caused by proteolytic activity.

8 Claims, No Drawings

SEQUENCE LISTING

```
<160> NUMBER OF SEQ ID NOS: 3

<210> SEQ ID NO 1
<211> LENGTH: 9
<212> TYPE: PRT
<213> ORGANISM: Artificial Sequence
<220> FEATURE:
<223> OTHER INFORMATION: A synthetic peptide

<400> SEQUENCE: 1

Cys Thr Lys Ser Ile Pro Pro Ile Cys
 1               5
```

```
<210> SEQ ID NO 2
<211> LENGTH: 14
<212> TYPE: PRT
<213> ORGANISM: Artificial Sequence
<220> FEATURE:
<223> OTHER INFORMATION: A synthetic peptide

<400> SEQUENCE: 2

Gly Arg Cys Thr Lys Ser Ile Pro Pro Ile Cys Phe Pro Asp
 1               5                  10

<210> SEQ ID NO 3
<211> LENGTH: 13
<212> TYPE: PRT
<213> ORGANISM: Artificial Sequence
<220> FEATURE:
<223> OTHER INFORMATION: A synthetic peptide

<400> SEQUENCE: 3

Ile Pro Pro Ile Cys Phe Pro Asp Gly Arg Cys Thr Lys
 1               5                  10
```

COMPOSITIONS OF SUNFLOWER TRYPSIN INHIBITORS

FIELD OF THE INVENTION

The present invention relates to compositions and articles containing protease inhibitors relating to sunflower trypsin inhibitor-1.

BACKGROUND OF THE INVENTION

The skin acts as the body's first line of defense against infection. However, the skin can become irritated and loose its ability to defend against infection by continual exposure to proteases. For example, it was once believed that contacting the skin with urine produced diaper rash. However, it is now understood that the irritation of tissue that manifests itself in "diaper rash" is primarily caused by proteolytic and/or lipolytic enzymes that are present in human feces, for example, trypsin, chymotrypsin, elastase, and pancreatic lipase. Moreover, the causes of skin irritation are not limited to enzymes present in feces. Other biological materials including, for example, menstrual fluids, nasal fluids, colostomy fluids, dandruff, wound healing may all provide a source of enzymes that produce skin irritation.

While some proteolytic and lipolytic enzyme inhibitors are known, they often have short-lived effects and/or can irritate skin and other tissues. Hence, compositions containing naturally-occurring, stable and non-irritating protease inhibitors are needed for use in personal care items such as diapers, tampons and feminine care pads.

SUMMARY OF THE INVENTION

The present invention relates to the prevention of pernicious and otherwise unwanted skin conditions, such as rashes and irritations that are caused by contact with proteolytic and/or lipolytic enzymes. For example, among the conditions that the present invention seeks to ameliorate is diaper rash. The compositions and methods of the invention utilize cyclic peptides as inhibitors of proteases to prevent such rashes and irritations.

In general, the cyclic peptides of the invention are recognized and bound by a serine proteases but are not cleaved by the serine protease. Such cyclic peptides can inhibit serine protease activity. For example, cyclic peptides of the invention can inhibit protease activity by trypsin, β-trypsin, chymotrypsin, cathepsin G, aminopeptidase, elastase, matripase, or thrombin.

In one embodiment, the invention provides a composition suitable for treatment of the dermis that includes a dermatologically acceptable carrier and an effective amount of a cyclic peptide having an amino acid sequence of any one of formulae I–III:

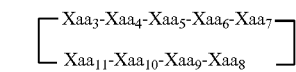

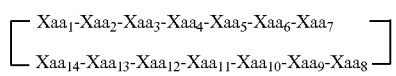

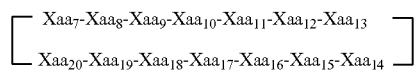

wherein:
each $Xaa_1$, $Xaa_8$, $Xaa_9$, $Xaa_{13}$ and $Xaa_{15}$ is separately a nonpolar amino acid;
each $Xaa_2$ and $Xaa_5$ is separately a basic amino acid;
each $Xaa_3$, $Xaa_{11}$ and $Xaa_{17}$ is separately a cysteine-like amino acid;
each $Xaa_4$ $Xaa_6$ and $Xaa_{18}$ is separately a polar amino acid;
each $Xaa_7$ and $Xaa_{10}$ is separately an aliphatic or a neutral polar amino acid;
$Xaa_{12}$ is an aromatic amino acid;
$Xaa_{14}$ is an acidic amino acid; and
each $Xaa_{16}$ and $Xaa_{19}$ is separately a basic amino acid.

In certain peptides, $Xaa_{12}$ is phenylalanine or tryptophan; $Xaa_3$ and $Xaa_{11}$ are cysteine; and $Xaa_5$ is lysine.

Examples of specific peptides of the invention include cyclic peptides having amino acid sequences SEQ ID NO:1 (CTKSIPPIC), SEQ ID NO:2 (GRCTKSIPPICFPD) or SEQ ID NO:3 (IPPICFPDGRCTK). A mixture of cyclic peptides can also be used in the compositions of the invention.

The invention also provides a method for treating or preventing a skin irritation on a mammal that involves administering to the mammal a composition containing a dermatologically acceptable carrier and an effective amount of a cyclic peptide having an amino acid sequence of formula I, formula II or formula III. Such a skin irritation can primarily be caused by proteolytic enzymes that are present in human feces, menstrual fluids, nasal fluids, colostomy fluids, dandruff, or healing wounds.

The invention further provides an absorbent article that includes one or more cyclic peptides of the invention. Such an absorbent article can, for example, be a feminine hygiene garment, a sanitary napkin, a panty liner, a tampon, a diaper, an incontinence brief, or a pair of training pants.

DETAILED DESCRIPTION OF THE INVENTION

The present invention provides small cyclic peptides, compositions and articles that can inhibit or prevent skin irritation caused by proteolytic activity. Target proteases against which the present cyclic peptides are effective include serine proteases such trypsin, β-trypsin, chymotrypsin, cathepsin G, elastase, matripase, thrombin and the like.

Definitions

The term "amino acid," includes the residues of the natural α-amino acids (e.g. Ala, Arg, Asn, Asp, Cys, Glu, Gln, Gly, His, Hyl, Hyp, Ile, Leu, Lys, Met, Phe, Pro, Ser, Thr, Trp, Tyr, and Val) in D or L form, as well as β-amino acids, synthetic and unnatural amino acids. Many types of amino acid residues are useful in the cyclic peptides and the invention is not limited to natural, genetically-encoded amino acids. Examples of amino acids that can be utilized in the cyclic peptide described herein can be found, for example, in Fasman, 1989, CRC Practical Handbook of Biochemistry and Molecular Biology, CRC Press, Inc., and the references cited therein. Another source of a wide variety of amino acid residues is provided by the website of RSP Amino Acids Analogues, Inc. (www.amino-acids.com). Amino acids of different types are further discussed below.

The term "mammal," as used herein, refers to an animal, in general, a warm-blooded animal, which is susceptible to or has a microbial infection. Mammals include cattle, buffalo, sheep, goats, pigs, horses, dogs, cats, rats, rabbits, mice, and humans. Also included are other livestock, domesticated animals and captive animals. The term "farm animals" includes chickens, turkeys, fish, and other farmed animals.

The term "peptide" as used herein includes a sequence of from five to twenty five amino acids residues in which the α-carboxyl group of one amino acid is joined by an amide bond to the main chain (α- or β-) amino group of the adjacent amino acid. The peptides provided herein for use in the described and claimed methods and compositions are cyclic. Peptide sequences specifically recited herein are written with the amino terminus on the left and the carboxy terminus on the right. However, where the peptides are shown in cyclic form, the first amino acid in the sequence is arbitrarily chosen. Moreover, for formulae of cyclic peptides where the sequence extends onto two lines, the sequence on the second line extends from the N-terminal side on the right to the C-terminal side on the left.

The term "substantially no" with reference to toxicity, or the like, means that little or no toxicity, or the like, is present at the tested or desired peptide dosage or concentration. By way of example, "substantially no" toxicity can mean that less than about 20%, alternatively less than 15% or less than 10%, or no detectable, cell toxicity or cell death is observed at the tested or desired peptide dosage or concentration. In other embodiments, "substantially no" toxicity means that less than about 5%, or no detectable, toxicity is observed at the tested or desired peptide dosage or concentration.

The term "therapeutically effective amount" is that amount sufficient to control a skin irritation or rash. A therapeutically effective amount generally controls the amount of irritation, for example, in at least about 20%, in at least about 40%, in at least about 60%, or in at least about 80% of treated subjects relative to untreated subjects. In some embodiments, a therapeutically effective amount controls the amount of irritation in at least about 90% or more of patients. These percentages refer to a decrease in the area of skin irritation found in the mammal and/or the decrease in symptoms associated with an irritation characterized by the presence of protease on the treated subject relative to untreated subjects. An effective amount of the therapeutic agent necessary to control skin irritation can vary according to factors such as the type of protease, the amount of proteases already present in the animal, the age, sex, health and weight of the mammal, and the ability of the cyclic peptides of the present invention to control protease activity on the mammal. Therapeutically effective amounts of the peptide and peptide compositions can also be used to prevent a recurrence of skin irritation.

Cyclic Peptide Inhibitors

The present invention provides cyclic peptides as well as compositions and articles having cyclic peptides. The cyclic peptides of the invention have amino acid sequences that are recognized and bound by serine proteases but are not cleaved by such serine proteases. Serine proteases that can bind but not cleave the present cyclic peptides include serine proteases such trypsin, β-trypsin, chymotrypsin, cathepsin G, aminopeptidase, elastase, matripase, thrombin and the like.

The cyclic peptides of the invention are between about five to about twenty five, alternatively about six to about twenty amino acids in length.

Amino acids used in the cyclic peptides can be genetically encoded amino acids, naturally occurring non-genetically encoded amino acids, or synthetic amino acids. Both L- and D-enantiomers of any of the above are utilized in the cyclic peptides. The amino acid notations used herein for the twenty genetically encoded L-amino acids and some examples of non-encoded amino acids are provided in Table 1.

TABLE 1

| Amino Acid | One-Letter Symbol | Common Abbreviation |
|---|---|---|
| Alanine | A | Ala |
| Arginine | R | Arg |
| Asparagine | N | Asn |
| Aspartic acid | D | Asp |
| Cysteine | C | Cys |
| Glutamine | Q | Gln |
| Glutamic acid | E | Glu |
| Glycine | G | Gly |
| Histidine | H | His |
| Isoleucine | I | Ile |
| Leucine | L | Leu |
| Lysine | K | Lys |
| Methionine | M | Met |
| Phenylalanine | F | Phe |
| Proline | P | Pro |
| Serine | S | Ser |
| Threonine | T | Thr |
| Tryptophan | W | Trp |
| Tyrosine | Y | Tyr |
| Valine | V | Val |
| B-Alanine | | Bala |
| 2,3-Diaminopropionic acid | | Dpr |
| A-Aminoisobutyric acid | | Aib |
| N-Methylglycine (sarcosine) | | MeGly |
| Ornithine | | Orn |
| Citrulline | | Cit |
| t-Butylalanine | | t-BuA |
| t-Butylglycine | | t-BuG |
| N-methylisoleucine | | MeIle |
| Phenylglycine | | Phg |
| Cyclohexylalanine | | Cha |
| Norleucine | | Nle |
| Naphthylalanine | | Nal |
| Pyridylalanine | | |
| 3-Benzothienyl alanine | | |
| 4-Chlorophenylalanine | | Phe(4-Cl) |
| 2-Fluorophenylalanine | | Phe(2-F) |
| 3-Fluorophenylalanine | | Phe(3-F) |
| 4-Fluorophenylalanine | | Phe(4-F) |
| Penicillamine | | Pen |
| 1,2,3,4-Tetrahydro-isoquinoline-3-carboxylic acid | | Tic |
| B-2-thienylalanine | | Thi |
| Methionine sulfoxide | | MSO |
| Homoarginine | | Harg |
| N-acetyl lysine | | AcLys |
| 2,4-Diamino butyric acid | | Dbu |
| P-Aminophenylalanine | | Phe(pNH$_2$) |
| N-methylvaline | | MeVal |
| Homocysteine | | Hcys |
| Homoserine | | Hser |
| E-Amino hexanoic acid | | Aha |
| Δ-Amino valeric acid | | Ava |
| 2,3-Diaminobutyric acid | | Dab |

Certain commonly encountered amino acids that are not genetically encoded and that can be present in the cyclic peptides of the invention include, but are not limited to, β-alanine (b-Ala) and other omega-amino acids such as 3-aminopropionic acid (Dap), 2,3-diaminopropionic acid (Dpr), 4-aminobutyric acid and so forth; α-aminoisobutyric acid (Aib); ε-aminohexanoic acid (Aha); δ-aminovaleric acid (Ava); methylglycine (MeGly); ornithine (Orn); citrulline (Cit); t-butylalanine (t-BuA); t-butylglycine (t-BuG); N-methylisoleucine (MeIle); phenylglycine (Phg); cyclohexylalanine (Cha); norleucine (Nle); 2-naphthylalanine (2-Nal); 4-chlorophenylalanine (Phe(4-Cl)); 2-fluorophenylalanine (Phe(2-F)); 3-fluorophenylalanine (Phe(3-F)); 4-fluorophenylalanine (Phe(4-F)); penicillamine (Pen); 1,2,3,4-tetrahydroisoquinoline-3-carboxylic acid (Tic); .beta.-2-thienylalanine (Thi); methionine sulfoxide (MSO); homoarginine (hArg); N-acetyl lysine (AcLys); 2,3-diaminobutyric acid (Dab); 2,3-diaminobutyric acid (Dbu); p-aminophenylalanine (Phe(pNH$_2$)); N-methyl valine (MeVal); homocysteine (hCys) and homoserine (hSer). Additional amino acid analogs contemplated include phosphoserine, phosphothreonine, phosphotyrosine, hydroxyproline, gamma-carboxyglutamate, hippuric acid, octahydroindole-2-carboxylic acid, statine, α-methyl-alanine, para-benzoylphenylalanine, propargylglycine, and sarcosine. Peptides that are encompassed within the scope of the invention can have any of foregoing amino acids in the L- or D-configuration, or any other amino acid known to one of skill in the art.

Amino acids that are substitutable for each other generally reside within similar classes or subclasses. As known to one of skill in the art, amino acids can be placed into different classes depending primarily upon the chemical and physical properties of the amino acid side chain. For example, some amino acids are generally considered to be hydrophilic or polar amino acids and others are considered to be hydrophobic or nonpolar amino acids. Polar amino acids include amino acids having acidic, basic or hydrophilic side chains and nonpolar amino acids include amino acids having aromatic or hydrophobic side chains. Nonpolar amino acids may be further subdivided to include, among others, aliphatic amino acids. The definitions of the classes of amino acids as used herein are as follows:

"Nonpolar Amino Acid" refers to an amino acid having a side chain that is uncharged at physiological pH, that is not polar and that is generally repelled by aqueous solution. Examples of genetically encoded hydrophobic amino acids include Ala, Ile, Leu, Met, Trp, Tyr and Val. Examples of non-genetically encoded nonpolar amino acids include t-BuA, Cha and Nle.

"Aromatic Amino Acid" refers to a nonpolar amino acid having a side chain containing at least one ring with a conjugated π-electron system (aromatic group). The aromatic group may be further substituted with substituent groups such as alkyl, alkenyl, alkynyl, hydroxyl, sulfonyl, nitro and amino groups, as well as others. Examples of genetically encoded aromatic amino acids include phenylalanine, tyrosine and tryptophan. Commonly encountered non-genetically encoded aromatic amino acids include phenylglycine, 2-naphthylalanine, β-2-thienylalanine, 1,2,3,4-tetrahydroisoquinoline-3-carboxylic acid, 4-chlorophenylalanine, 2-fluorophenylalanine, 3-fluorophenylalanine and 4-fluorophenylalanine.

"Aliphatic Amino Acid" refers to a nonpolar amino acid having a saturated or unsaturated straight chain, branched or cyclic hydrocarbon side chain. Examples of genetically encoded aliphatic amino acids include Ala, Leu, Val and Ile. Examples of non-encoded aliphatic amino acids include Nle.

"Polar Amino Acid" refers to a hydrophilic amino acid having a side chain that is charged or uncharged at physiological pH and that has a bond in which the pair of electrons shared in common by two atoms is held more closely by one of the atoms. Polar amino acids are generally hydrophilic, meaning that they have an amino acid having a side chain that is attracted by aqueous solution. Examples of genetically encoded polar amino acids include asparagine, cysteine, glutamine, lysine and serine. Examples of non-genetically encoded polar amino acids include citrulline, homocysteine, N-acetyl lysine and methionine sulfoxide.

"Acidic Amino Acid" refers to a hydrophilic amino acid having a side chain pK value of less than 7. Acidic amino acids typically have negatively charged side chains at physiological pH due to loss of a hydrogen ion. Examples of genetically encoded acidic amino acids include aspartic acid (aspartate) and glutamic acid (glutamate).

"Basic Amino Acid" refers to a hydrophilic amino acid having a side chain pK value of greater than 7. Basic amino acids typically have positively charged side chains at physiological pH due to association with hydronium ion. Examples of genetically encoded basic amino acids include arginine, lysine and histidine. Examples of non-genetically encoded basic amino acids include the non-cyclic amino acids ornithine, 2,3-diaminopropionic acid, 2,4-diaminobutyric acid and homoarginine.

"Ionizable Amino Acid" refers to an amino acid that can be charged at a physiological pH. Such ionizable amino acids include acidic and basic amino acids, for example, D-aspartic acid, D-glutamic acid, D-histidine, D-arginine, D-lysine, D-hydroxylysine, D-ornithine, L-aspartic acid, L-glutamic acid, L-histidine, L-arginine, L-lysine, L-hydroxylysine or L-ornithine.

As will be appreciated by those having skill in the art, the above classifications are not absolute. Several amino acids exhibit more than one characteristic property, and can therefore be included in more than one category. For example, tyrosine has both a nonpolar aromatic ring and a polar hydroxyl group. Thus, tyrosine has several characteristics that could be described as nonpolar, aromatic and polar. However, the nonpolar ring is dominant and so tyrosine is generally considered to be nonpolar. Similarly, in addition to being able to form disulfide linkages, cysteine also has nonpolar character. Thus, while not strictly classified as a hydrophobic or nonpolar amino acid, in many instances cysteine can be used to confer hydrophobicity or nonpolarity to a peptide.

The classifications of the above-described genetically encoded and non-encoded amino acids are summarized in Table 2, below. It is to be understood that Table 2 is for illustrative purposes only and does not purport to be an exhaustive list of amino acid residues that may comprise the peptides described herein. Other amino acid residues that are useful for making the peptides described herein can be found, e.g., in Fasman, 1989, CRC Practical Handbook of Biochemistry and Molecular Biology, CRC Press, Inc., and the references cited therein. Another source of amino acid residues is provided by the website of RSP Amino Acids Analogues, Inc. (www.amino-acids.com). Amino acids not specifically mentioned herein can be conveniently classified into the above-described categories on the basis of known behavior and/or their characteristic chemical and/or physical properties as compared with amino acids specifically identified.

TABLE 2

| Classification | Genetically Encoded | Genetically Non-Encoded |
|---|---|---|
| Nonpolar | | |
| Aromatic | F, Y, W | Phg, Nal, Thi, Tic, Phe(4-Cl), Phe(2-F), Phe(3-F), Phe(4-F), Pyridyl Ala, Benzothienyl Ala |
| Aliphatic | A, V, L, I | t-BuA, t-BuG, MeIle, Nle, MeVal, Cha, bAla, MeGly, Aib |
| Other Nonpolar | M, G, P | |
| Polar | | |
| Acidic | D, E | |
| Basic | H, K, R | Dpr, Orn, hArg, Phe(p-NH$_2$), DBU, A$_2$ BU |
| Neutral Polar | S, T, Y, Q, N, D, E, H, R, K, C | Cit, AcLys, MSO, hSer, Orn, Hcys |
| Cysteine-Like | C | Pen, hCys, β-methyl Cys |

In some embodiments, polar amino acids contemplated by the present invention include, for example, arginine, asparagine, aspartic acid, cysteine, glutamic acid, glutamine, histidine, homocysteine, lysine, hydroxylysine, ornithine, serine, threonine, and structurally related amino acids. In one embodiment the polar amino is an ionizable amino acid such as arginine, aspartic acid, glutamic acid, histidine, hydroxylysine, lysine, or ornithine.

Examples of nonpolar or nonpolar amino acid residues that can be utilized include, for example, alanine, valine, leucine, methionine, isoleucine, phenylalanine, tryptophan, tyrosine and the like.

In addition, the amino acid sequence of a peptide can be modified so as to result in a peptide variant that includes the substitution of at least one amino acid residue in the peptide for another amino acid residue, including substitutions that utilize the D rather than L form.

One or more of the residues of the peptide can be exchanged for another, to alter, enhance or preserve the biological activity of the peptide. Such a variant can have, for example, at least about 10%, 20%, 30%, 40%, 50%, 60%, 70%, 80%, 90%, 95% or 99% of the inhibitory activity of the corresponding non-variant peptide. Conservative amino acid substitutions are often utilized, for example, substitutions of amino acids with similar chemical and physical properties, as described above.

Hence, for example, conservative amino acids substitutions involve exchanging aspartic acid for glutamic acid; exchanging lysine for arginine or histidine; exchanging one nonpolar amino acid (alanine, isoleucine, leucine, methionine, phenylalanine, tryptophan, tyrosine, valine,) for another; and exchanging one polar amino acid (aspartic acid, asparagine, glutamic acid, glutamine, glycine, serine, threonine, etc.) for another. After the substitutions are introduced, the variants are screened for biological activity, for example, by observing whether the peptide inhibits a serine protease.

In one embodiment, the cyclic peptides of the invention can have an amino acid sequence relating to formula I:

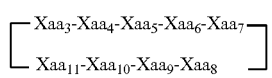

I wherein:
each Xaa$_3$ and Xaa$_{11}$ is separately a cysteine-like amino acid;
each Xaa$_4$ and Xaa$_6$; is separately a polar amino acid;
Xaa$_5$ is a basic amino acid;
each Xaa$_7$ and Xaa$_{10}$ is separately an aliphatic or a neutral polar amino acid; and
each Xaa$_8$ and Xaa$_9$ is separately a nonpolar amino acid.

In some embodiments, the peptide inhibitor is a cyclic peptide having SEQ ID NO:1 (CTKSIPPIC).

In another embodiment, the cyclic peptides of the invention can have an amino acid sequence having formula II:

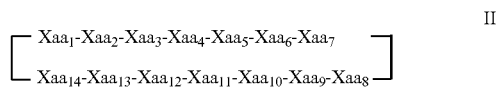

II wherein:
each Xaa$_1$, Xaa$_8$, Xaa$_9$ and Xaa$_{13}$ is separately a nonpolar amino acid;
each Xaa$_2$ and Xaa$_5$ is separately a basic amino acid;
each Xaa$_3$ and Xaa$_{11}$ is separately a cysteine-like amino acid;
each Xaa$_4$ and Xaa$_6$ is separately a polar amino acid;
each Xaa$_7$ and Xaa$_{10}$ is separately an aliphatic or a neutral polar amino acid;
Xaa$_{12}$ is an aromatic amino acid; and
Xaa$_{14}$ is an acidic amino acid.

In some embodiments, Xaa$_{12}$ is phenylalanine or tryptophan; Xaa$_3$ and Xaa$_{11}$ are cysteine; and Xaa$_5$ is lysine. One example of a peptide inhibitor of the invention is a cyclic peptide having SEQ ID NO:2(GRCTKSIPPICFPD).

In another embodiment, the cyclic peptides of the invention can have an amino acid sequence having formula III:

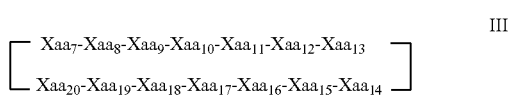

III wherein:
each Xaa$_7$ and Xaa$_{10}$ is separately an aliphatic or a neutral polar amino acid;
each Xaa$_8$, Xaa$_9$, Xaa$_{13}$ and Xaa$_{15}$ is separately a nonpolar amino acid;
each Xaa$_{11}$ and Xaa$_{17}$ is separately a cysteine-like amino acid;
Xaa$_{12}$ is an aromatic amino acid;
Xaa$_{14}$ is an acidic amino acid;
each Xaa$_{16}$ and Xaa$_{19}$ is separately a basic amino acid; and
Xaa$_{18}$ is a polar amino acid.

In some embodiments, Xaa$_{12}$ is phenylalanine or tryptophan; Xaa$_{11}$ and Xaa$_{17}$ are cysteine; Xaa$_{16}$ is arginine; and Xaa$_{19}$ is lysine. In some embodiments, the peptide inhibitor is a cyclic peptide having SEQ ID NO:3(IPPICFDGRCTK).

The cyclic peptides of the present invention, for example, include any of peptide having any of formulae I, II or III. In some embodiments the cyclic peptides employed are those with SEQ ID NO:1, 2 or 3. Formulations or compositions containing the present cyclic peptides can include a mixture of two or more cyclic peptides.

The present isolated, purified peptides or variants thereof, can be synthesized in vitro, e.g., by the solid phase peptide synthetic method or by enzyme catalyzed peptide synthesis or with the aid of recombinant DNA technology. Solid phase peptide synthetic method is an established and widely used method, which is described in references such as the following: Stewart et al., *Solid Phase Peptide Synthesis*, W. H. Freeman Co., San Francisco (1969); Merrifield, *J. Am. Chem. Soc.* 85 2149 (1963); Meienhofer in "Hormonal Proteins and Peptides," ed.; C.H. Li, Vol.2 (Academic Press, 1973), pp.48–267; and Bavaay and Merrifield, "The Peptides," eds. E. Gross and F. Meienhofer, Vol.2 (Academic Press, 1980) pp.3–285. These peptides can be further purified by fractionation on immunoaffinity or ion-exchange columns; ethanol precipitation; reverse phase HPLC; chromatography on silica or on an anion-exchange resin such as DEAE; chromatofocusing; SDS-PAGE; ammonium sulfate precipitation; gel filtration using, for example, Sephadex G-75; ligand affinity chromatography; or crystallization or precipitation from non-polar solvent or nonpolar/polar solvent mixtures. In some embodiments the peptides are purified by crystallization or precipitation.

To identify highly active cyclic peptides that can inhibit serine proteases with little or no undesired toxicity for mammalian cells, individual cyclic peptides, or libraries of cyclic peptides can be made and the individual cyclic peptides or cyclic peptides from those libraries can be screened for inhibitory activity and lack of toxicity. For example, libraries of peptides can be made using a one-bead-one-compound strategy provided by Lam et al. (97 Chem. Rev. 411–448 (1997) or synthesized on macrobeads by a split and pool method of Furka, et al. (37 Int. J. Pept. Prot. Res. 487–493(1991)). Mass spectrometric sequence analysis techniques enable rapid identification of every peptide within a given library. See, Biemann, K. 193 Methods Enzymol. 455 (1990). In general, synthetic operations, including peptide cyclization, are performed on solid support to avoid laborious and difficult to automate solution-phase operations. Moreover, the final product of the synthesis regimen is generally sufficiently pure for biological assays without laborious purification procedures. Peptide yields from each synthesis can be sufficient for performing 50 to 100 assays. Rapid, automatic mass-spectrometry-based peptide sequence analysis can be performed to identify peptide sequences that have high activity and to discard peptide sequences with low activity.

The synthetic approach employed can provide individually separable and identifiable peptide sequences to avoid the use of combinatorial library mixtures and laborious deconvolution techniques. However, libraries of impure mixtures of peptides can also be generated for testing. Impure preparations of peptides can be used for quick screening of combinations of sequences. When a mixture of peptides shows activity, the peptides in the mixture can either be individually isolated and tested or pure peptides having sequences known to be present in the impure mixture can be individually prepared and tested.

N-acyl derivatives of an amino group of the peptide or peptide variants may be prepared by utilizing an N-acyl protected amino acid for the final condensation, or by acylating a protected or unprotected peptide. O-acyl derivatives may be prepared, for example, by acylation of a free hydroxy peptide or peptide resin. Either acylation may be carried out using standard acylating reagents such as acyl halides, anhydrides, acyl imidazoles, and the like. Both N-acylation and O-acylation may be carried out together, if desired.

Salts of carboxyl groups of a peptide or peptide variant of the invention may be prepared in the usual manner by contacting the peptide with one or more equivalents of a desired base such as, for example, a metallic hydroxide base, e.g., sodium hydroxide; a metal carbonate or bicarbonate base such as, for example, sodium carbonate or sodium bicarbonate; or an amine base such as, for example, triethylamine, triethanolamine, and the like.

Acid addition salts of the peptide or variant peptide, or of amino residues of the peptide or variant peptide, may be prepared by contacting the peptide or amine with one or more equivalents of the desired inorganic or organic acid, such as, for example, hydrochloric acid. Esters of carboxyl groups of the peptides may also be prepared by any of the usual methods known in the art.

Effects of the Compositions on Skin Tissues

The compositions and methods of the invention are useful for protecting and soothing skin tissues by inhibiting protease activity. The compositions of the present invention are also useful for regulating the condition of skin. Regulation of skin conditions, namely mammalian and, in particular, human skin conditions, is often required due to conditions that may be induced or caused by factors internal and/or external to the body. Examples include, exposure to feces, urine, blood, ultraviolet radiation, stress, diseases, etc.

Regulating the skin condition may involve one or more of the following benefits: increasing the rate of skin renewal, thickening the skin (i.e., building the epidermis, dermis, sub-dermal, subcutaneous fat, or underlying muscle layers of the skin) to reduce skin atrophy. The compositions and methods of the invention can also decrease the incidence of rashes and irritations such as diaper rash. As used herein, therapeutically regulating skin condition includes ameliorating, e.g., healing, diminishing, minimizing, and inhibiting discontinuities, rashes and irritations in skin.

Additional Ingredients

In some embodiments, the peptides of the present invention are provided in a composition with a skin care carrier ("carrier"). In addition to its function as a vehicle for delivering an effective concentration of a cyclic peptide to a user's skin, the peptide compositions may also comprise ingredients that, for example, reduce the adherence of feces to skin, provide a skin-irritant barrier function, or provide other therapeutic benefits to the skin (e.g., improve skin softness, maintain or improve skin health), and the like.

The compositions of the present invention may therefore contain one or more additional skin care active ingredients.

In general, the additional components should be suitable for application to skin tissue, particularly when the composition is to be in contact with human keratinous tissue. Hence, the additional ingredients incorporated into the composition are suitable for contact with human skin tissue and do out have undue toxicity, incompatibility, instability, allergic response, and the like within the scope of sound medical judgment.

The CTFA Cosmetic Ingredient Handbook, Second Edition (1992) describes a wide variety of non-limiting cosmetic and pharmaceutical ingredients commonly used in the skin care industry, which are suitable for use in the compositions of the present invention. Examples of these ingredient classes include: abrasives, absorbents, aesthetic components such as fragrances, pigments, colorings/colorants, essential oils, skin sensates, astringents (clove oil, menthol, camphor, eucalyptus oil, eugenol, menthyl lactate, witch hazel distillate), anti-acne agents, anti-caking agents, anti-foaming agents, antimicrobial agents, antioxidants, binders, biological additives, buffering agents, bulking agents, chelating agents, chemical additives, colorants, cosmetic astringents, cosmetic biocides, denaturants, drug astringents, external analgesics, film formers, opacifying agents, pH adjusters, propellants, reducing agents, sequestrants, skin bleaching and lightening agents (e.g., hydroquinone, kojic acid, ascorbic acid, magnesium ascorbyl phosphate, ascorbyl glucosamine), skin-conditioning agents (e.g., humectants, including miscellaneous and occlusive), skin soothing and/or healing agents (e.g., panthenol and panthenol derivatives), aloe vera, pantothenic acid, pantothenic acid derivatives, allantoin, bisabolol, and dipotassium glycyrrhizinate, skin treating agents, thickeners, and vitamins and derivatives thereof.

In any embodiment of the present invention, however, the active ingredients useful herein can be categorized by the benefit they provide or by their postulated mode of action. However, it is to be understood that the active ingredients useful herein can in some instances provide more than one benefit or operate via more than one mode of action. Therefore, classifications herein are made for the sake of convenience and are not intended to limit the active ingredients to that particular application or applications listed.

Desquamation Compounds

A safe and effective amount of a desquamation compound may be added to the compositions of the present invention, or from about 0.1% to about 10%, or from about 0.2% to about 5%, or from about 0.5% to about 4%, by weight of the composition. Desquamation compounds enhance the skin appearance benefits of the present invention. For example, the desquamation compounds tend to improve the texture of the skin (e.g., smoothness). One desquamation system that is suitable for use herein contains sulfhydryl compounds and zwitterionic surfactants and is described in U.S. Pat. No. 5,681,852, to Bissett, incorporated herein by reference. Zwitterionic surfactants such as described in these applications are also useful as desquamatory agents herein, with cetyl betaine being particularly desirable.

Anti-Acne Ingredients

The compositions of the present invention may contain a safe and effective amount of one or more anti-acne active ingredients. Examples of useful anti-acne ingredients include resorcinol, sulfur, benzoyl peroxide, erythromycin, zinc, and the like. Further examples of suitable anti-acne compounds are described in further detail in U.S. Pat. No. 5,607,980, issued to McAtee et al, on Mar. 4, 1997.

Anti-Wrinkle Compounds/Anti-Atrophy Compounds

The compositions of the present invention may further contain a safe and effective amount of one or more anti-wrinkle compounds or anti-atrophy compounds. Exemplary anti-wrinkle/anti-atrophy compounds suitable for use in the compositions of the present invention include sulfur-containing D and L amino acids and their derivatives and salts, particularly the N-acetyl derivatives, a preferred example of which is N-acetyl-L-cysteine; thiols (e.g. ethane thiol); phytic acid, lipoic acid; lysophosphatidic acid, skin peel agents (e.g., phenol and the like), vitamin $B_3$ compounds and retinoids that enhance the health and/or appearance of skin tissues.

Vitamin $B_3$ Compounds

The compositions of the present invention may contain a safe and effective amount of a vitamin $B_3$ compound. When vitamin $B_3$ compounds are present in the compositions of the instant invention, the compositions can contain from about 0.01% to about 50%, or from about 0.1% to about 10%, or from about 0.5% to about 10%, or from about 1% to about 5%, or from about 2% to about 5%, by weight of the composition, of the vitamin $B_3$ compound.

As used herein, "vitamin $B_3$ compound" means a compound having the formula:

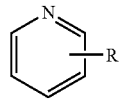

wherein R is —$CONH_2$ (e.g., niacinamide), —COOH (e.g., nicotinic acid) or —$CH_2OH$ (e.g., nicotinyl alcohol), derivatives thereof, and salts of any of the foregoing. Exemplary derivatives of the foregoing vitamin $B_3$ compounds include nicotinic acid esters, including non-vasodilating esters of nicotinic acid (e.g., tocopheryl nicotinate), nicotinyl amino acids, nicotinyl alcohol esters of carboxylic acids, nicotinic acid N-oxide and niacinamide N-oxide.

The vitamin compounds may be included as substantially pure compounds, or as extracts obtained by suitable physical and/or chemical isolation from natural (e.g., plant) sources.

Examples of suitable vitamin $B_3$ compounds are well known in the art and are commercially available from a number of sources, e.g., the Sigma Chemical Company (St. Louis, Mo.); ICN Biomedicals, Inc. (Irvin, Calif.) and Aldrich Chemical Company (Milwaukee, Wis.).

Retinoids

The compositions of the present invention may also contain a retinoid. As used herein, "retinoid" includes all natural and/or synthetic analogs of Vitamin A or retinol-like compounds that possess the biological activity of Vitamin A in the skin as well as the geometric isomers and stereoisomers of these compounds. The retinoid can, for example, be retinol, retinol esters (e.g., $C_2$–$C_{22}$ alkyl esters of retinol, including retinyl palmitate, retinyl acetate, and retinyl propionate), retinal, and/or retinoic acid (including all-trans retinoic acid and/or 13-cis-retinoic acid). In some embodiments, retinoids other than retinoic acid are used. These compounds are available in the art and are commercially available from a number of sources, e.g., Sigma Chemical Company (St. Louis, Mo.), and Boerhinger Mannheim (Indianapolis, Ind.). Other retinoids that are useful herein are described in U.S. Pat. No. 4,677,120, issued Jun. 30, 1987 to Parish et al.; U.S. Pat. No. 4,885,311, issued Dec. 5, 1989 to Parish et al.; U.S. Pat. No. 5,049,584, issued Sep. 17, 1991 to Purcell et al.; U.S. Pat. No. 5,124,356, issued Jun. 23, 1992 to Purcell et al.; and U.S. Pat. Reissue 34,075, issued Sep. 22, 1992 to Purcell et al. Other suitable retinoids are tocopheryl-retinoate, tocopherol ester of cis- or trans-retinoic acid, adapalene (6-[3-(1-adamantyl)-4-methoxyphenyl]-2-naphthoic acid), and tazarotene (ethyl 6-[2-(4,4-dimethylthiochroman-6-yl)-ethynyl]nicotinate). Desirable retinoids include retinol, retinyl palmitate, retinyl acetate, retinyl propionate, retinal and combinations thereof.

The retinoid may be included as a substantially pure compound, or as an extract obtained by suitable physical and/or chemical isolation from natural (e.g., plant) sources. In some embodiments, the retinoid is substantially pure, or essentially pure.

The compositions of this invention may contain a safe and effective amount of the retinoid, such that the resultant composition is safe and effective for regulating or improving the condition of skin tissues. The compositions and methods of the invention can improve visible and/or tactile discontinuities in skin, or improve signs of skin aging. The compositions preferably contain from about 0.005% to about 2%, or from about 0.01% to about 2%, retinoid.

Retinol can also be used in an amount of from about 0.01% to about 0.15%. Retinol esters can be used in an amount of from or about 0.01% to or about 2% (e.g., about 1%). Retinoic acids can be used in an amount of from or about 0.01% to or about 0.25%. Tocopheryl-retinoate, adapalene, and tazarotene can be used in an amount of from or about 0.01% to or about 2%.

Where the compositions of the present invention contain both a retinoid and a vitamin $B_3$ compound, the retinoid can be used in the above amounts, and the vitamin $B_3$ compound can be used in an amount of from or about 0.1% to about 10%, or from about 2% to about 5%.

When included in the present compositions, peptides can be present in amounts of from about $1\times10^{-6}$% to about 10%, or from about $1\times10^{-6}$% to about 0.1%, or from about $1\times10^{-5}$% to about 0.01%, by weight of the composition. In certain compositions where the peptide is Carnosine™, the compositions can contain from about 0.1% to about 5%, by weight of the composition, of such peptides. In other embodiments wherein the peptide-containing compositions, Matrixyl™, and/or Biopeptide CL™ are included, the compositions can contain from about 0.1% to about 10%, by weight compositions, of Matrixyl™ and/or Biopeptide CL™ peptide-containing compositions.

Anti-Oxidants/Radical Scavengers

The compositions of the present invention may include a safe and effective amount of an anti-oxidant/radical scavenger. The anti-oxidant/radical scavenger is especially useful for providing protection against ultraviolet radiation that can cause increased scaling or texture changes in the stratum corneum and against other environmental agents that can cause skin damage.

A safe and effective amount of an anti-oxidant/radical scavenger may be added to the compositions of the subject invention, for example, from about 0.1% to about 10%, or from about 1% to about 5%, of the composition.

Anti-oxidants/radical scavengers such as ascorbic acid (vitamin C) and its salts, ascorbyl esters of fatty acids, ascorbic acid derivatives (e.g., magnesium ascorbyl phosphate, sodium ascorbyl phosphate, ascorbyl sorbate), tocopherol (vitamin E), tocopherol sorb ate, tocopherol acetate, other esters of tocopherol, butylated hydroxy benzoic acids and their salts, 6-hydroxy-2,5,7,8-tetramethylchroman-2-carboxylic acid (commercially available under the trade name Trolox™), gallic acid and its alkyl esters, especially propyl gallate, uric acid and its salts and alkyl esters, sorbic acid and its salts, lipoic acid, amines (e.g., N,N-diethylhydroxylamine, amino-guanidine), sulflhydryl compounds (e.g., glutathione), dihydroxy fumaric acid and its salts, lysine pidolate, arginine pilolate, nordihydroguaiaretic acid, bioflavonoids, curcumin, lysine, methionine, proline, superoxide dismutase, silymarin, tea extracts, grape skin/seed extracts, melanin, and rosemary extracts may be used. Other anti-oxidants/radical scavengers are selected from tocopherol sorbate and other esters of tocopherol. For example, the use of tocopherol sorbate in topical compositions and applicable to the present invention is described in U.S. Pat. No. 4,847,071.

Chelators

The compositions of the present invention may also contain a safe and effective amount of a chelator or chelating agent. As used herein, "chelator" or "chelating agent" means an active agent capable of removing a metal ion from a system by forming a complex so that the metal ion cannot readily participate in or catalyze chemical reactions. The inclusion of a chelating agent is useful for providing protection against ultraviolet radiation that can contribute to excessive scaling or skin texture changes and against other environmental agents that can cause skin damage.

A safe and effective amount of a chelating agent may be added to the compositions of the subject invention, for example, from about 0.1% to about 10%, or from about 1% to about 5%, of the composition. Exemplary chelators that are useful herein are disclosed in U.S. Pat. No. 5,487,884; International Publication No. 91/16035, Bush et al., published Oct. 31, 1995; and International Publication No. 91/16034, Bush et al., published Oct. 31, 1995. In some embodiments, the chelators used in compositions of the subject invention include, for example, firildioxime, furilmonoxime, and derivatives thereof.

Flavonoids

The compositions of the present invention may optionally contain a flavonoid compound. Flavonoids are broadly disclosed in U.S. Pat. Nos. 5,686,082 and 5,686,367, both of which are herein incorporated by reference. Flavonoids suitable for use in the present invention are flavanones selected from unsubstituted flavanones, mono-substituted flavanones, and mixtures thereof; chalcones selected from unsubstituted chalcones, mono-substituted chalcones, di-substituted chalcones, tri-substituted chalcones, and mixtures thereof; flavones selected from unsubstituted flavones, mono-substituted flavones, di-substituted flavones, and mixtures thereof; one or more isoflavones; coumarins selected from unsubstituted coumarins, mono-substituted coumarins, di-substituted coumarins, and mixtures thereof; chromones selected from unsubstituted chromones, mono-substituted chromones, di-substituted chromones, and mixtures thereof; one or more dicoumarols; one or more chromanones; one or more chromanols; isomers (e.g., cis/trans isomers) thereof; and mixtures thereof. By the term "substituted" as used herein means flavonoids wherein one or more hydrogen atom of the flavonoid has been independently replaced with hydroxyl, $C_1$–$C_8$ alkyl, $C_1$–$C_4$ alkoxyl, O-glycoside, and the like or a mixture of these substituents.

Examples of suitable flavonoids include, but are not limited to, unsubstituted flavanone, mono-hydroxy flavanones (e.g., 2'-hydroxy flavanone, 6-hydroxy flavanone, 7-hydroxy flavanone, etc.), mono-alkoxy flavanones (e.g., 5-methoxy flavanone, 6-methoxy flavanone, 7-methoxy flavanone, 4'-methoxy flavanone, etc.), unsubstituted chalcone (e.g. unsubstituted trans-chalcone), mono-hydroxy chalcones (e.g., 2'-hydroxy chalcone, 4'-hydroxy chalcone, etc.), di-hydroxy chalcones (e.g., 2',4-dihydroxy chalcone, 2',4'-dihydroxy chalcone, 2,2'-dihydroxy chalcone, 2',3-dihydroxy chalcone, 2',5'-dihydroxy chalcone, etc.), and trihydroxy chalcones (e.g., 2',3',4'-trihydroxy chalcone, 4,2',4'-trihydroxy chalcone, 2,2',4'-trihydroxy chalcone, etc.), unsubstituted flavone, 7,2'-dihydroxy flavone, 3',4'-dihydroxy naphthoflavone, 4'-hydroxy flavone, 5,6-benzoflavone, and 7,8-benzoflavone, unsubstituted isoflavone, daidzein (7,4'-dihydroxy isoflavone), 5,7-dihydroxy-4'-methoxy isoflavone, soy isoflavones (a mixture extracted from soy), unsubstituted coumarin, 4-hydroxy coumarin, 7-hydroxy coumarin, 6-hydroxy-4-methyl coumarin, unsubstituted chromone, 3-formyl chromone, 3-formyl-6-isopropyl chromone, unsubstituted dicoumarol, unsubstituted chromanone, unsubstituted chromanol, and mixtures thereof.

In some embodiments, unsubstituted flavanone, methoxy flavanones, unsubstituted chalcone, 2',4-dihydroxy chalcone, and mixtures thereof are used in the compositions of the invention. In other embodiments, unsubstituted flavanone, unsubstituted chalcone (especially the trans isomer), and mixtures thereof are used in the compositions of the invention.

Flavonoids can be synthesized or obtained as extracts from natural sources (e.g., plants). The naturally sourced material can also further be derivatized (e.g., an ester or ether derivative prepared following extraction from a natural source). Flavonoid compounds useful herein are also commercially available from a number of sources, e.g., Indofine Chemical Company, Inc. (Somerville, N.J.), Steraloids, Inc. (Wilton, N.H.), and Aldrich Chemical Company, Inc. (Milwaukee, Wis.). Mixtures of such flavonoid compounds may also be used.

The flavonoid compounds can be present in the invention, for example, at concentrations of from about 0.01% to about 20%, or from about 0.1% to about 10%, or from about 0.5% to about 5%.

Anti-Inflammatory Agents

A safe and effective amount of an anti-inflammatory agent may be added to the compositions of the present invention, for example, from about 0.1% to about 10%, or from about 0.5% to about 5%, of the composition. The anti-inflammatory agent can enhance the appearance of the skin, for example, by contributing to a more uniform and acceptable skin tone or color. The exact amount of anti-inflammatory agent to be used in the compositions will depend on the particular anti-inflammatory agent utilized since such agents vary widely in potency.

Steroidal anti-inflammatory agents, including but not limited to, corticosteroids such as hydrocortisone, hydroxyltriamcinolone, alpha-methyl dexamethasone, dexamethasone-phosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, diflurosone diacetate, fluradrenolone acetonide, medrysone, amcinafel, amcinafide, betamethasone and the balance of its esters, chloroprednisone, chlorprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof may be used. In some embodiments, the steroidal anti-inflammatory used is hydrocortisone.

A second class of anti-inflammatory agents that is useful in the compositions includes the nonsteroidal anti-inflammatory agents. A variety of compounds are encompassed by this group. For detailed disclosure of the chemical structure, synthesis, side effects, etc. of non-steroidal anti-inflammatory agents, one may refer to standard texts, including Anti-inflammatory and Anti-Rheumatic Drugs, K. D. Rainsford, Vol. I–III, CRC Press, Boca Raton, (1985), and Anti-inflammatory Agents, Chemistry and Pharmacology, 1, R. A. Scherrer, et al., Academic Press, New York (1974).

Specific non-steroidal anti-inflammatory agents useful in the composition invention include, but are not limited to:

1) the oxicams, such as piroxicam, isoxicam, tenoxicam, sudoxicam, and CP-14,304;
2) benorylate, trilisate, safapryn, solprin, diflunisal, and fendosal;
3) the acetic acid derivatives, such as diclofenac, fenclofenac, indomethacin, sulindac, tolmetin, isoxepac, furofenac, tiopinac, zidometacin, acematacin, fentiazac, zomepirac, clindanac, oxepinac, felbinac, and ketorolac;
4) the fenamates, such as mefenamic, meclofenamic, flufenamic, niflumic, and tolfenamic acids;
5) the propionic acid derivatives, such as ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, and tiaprofenic; and
6) the pyrazoles, such as phenylbutazone, oxyphenbutazone, feprazone, azapropazone, and trimethazone.

Mixtures of these non-steroidal anti-inflammatory agents may also be employed, as well as the dermatologically acceptable salts and esters of these agents. For example, etofenamate, a flufenamic acid derivative, is useful for topical application. Of the nonsteroidal anti-inflammatory agents, ibuprofen, naproxen, flufenamic acid, etofenamate, aspirin, mefenamic acid, meclofenamic acid, piroxicam and felbinac are often used. Ibuprofen, naproxen, ketoprofen, etofenamate, aspirin and flufenamic acid are frequently used.

Moreover, so-called "natural" anti-inflammatory agents are useful in methods of the present invention. Such agents may suitably be obtained as an extract by suitable physical and/or chemical isolation from natural sources (e.g., plants, fungi, by-products of microorganisms) or can be synthetically prepared. For example, candelilla wax, bisabolol (e.g., alpha bisabolol), aloe vera, plant sterols (e.g., phytosterol), Manjistha (extracted from plants in the genus *Rubia*, particularly *Rubia Cordifolia*), and *Guggal* (extracted from plants in the genus *Commiphora*, particularly *Commiphora Mukul*), kola extract, chamomile, red clover extract, and sea whip extract, may be used.

Additional anti-inflammatory agents useful herein include compounds of the Licorice (the plant genus/species *Glycyrrhiza glabra*) family, including glycyrrhetic acid, glycyrrhizic acid, and derivatives thereof (e.g., salts and esters). Suitable salts of the foregoing compounds include metal and ammonium salts. Suitable esters include $C_2$–$C_{24}$ saturated or unsaturated esters of the acids, or $C_{10}$–$C_{24}$, or $C_{16}$–$C_{24}$. Specific examples of the foregoing include oil soluble licorice extract, the glycyrrhizic and glycyrrhetic acids themselves, monoammonium glycyrrhizinate, monopotassium glycyrrhizinate, dipotassium glycyrrhizinate, 1-beta-glycyrrhetic acid, stearyl glycyrrhetinate, and 3-stearyloxy-glycyrrhetinic acid, and disodium 3-succinyloxy-beta-glycyrrhetinate. Stearyl glycyrrhetinate is preferred.

Topical Anesthetics

The compositions of the present invention may also contain a safe and effective amount of a topical anesthetic. Examples of topical anesthetic drugs include benzocaine, lidocaine, bupivacaine, chlorprocaine, dibucaine, etidocaine, mepivacaine, tetracaine, dyclonine, hexylcaine, procaine, cocaine, ketamine, pramoxine, phenol, and pharmaceutically acceptable salts thereof.

Skin Soothing and Skin Healing Compounds

The compositions of the present invention may comprise a skin soothing or skin-healing compound. Skin soothing or skin healing compounds suitable for use herein include panthenoic acid derivatives (including panthenol, dexpanthenol, and ethyl panthenol), aloe vera, allantoin, bisabolol, and dipotassium glycyrrhizinate. A safe and effective amount of a skin soothing or skin healing compound may be added to the present composition, for example, from about 0.1% to about 30%, or from about 0.5% to about 20%, or from about 0.5% to about 10%, by weight of the composition formed.

Anti-Microbial and Anti-Fungal Compounds

The compositions of the present invention may contain an anti-microbial or anti-fungal compound. Such compounds are capable of destroying microbes, preventing the development of microbes or preventing the pathogenic action of microbes. A safe and effective amount of an anti-microbial or anti-fungal compound may be added to the present compositions, for example, from about 0.001% to about 10%, or from about 0.01% to about 5%, or from about 0.05% to about 2%.

Examples of antimicrobial and antifungal compounds include β-lactam drugs, quinolone drugs, ciprofloxacin, norfloxacin, tetracycline, erythromycin, amikacin, 2,4,4'-trichloro-2'-hydroxy diphenyl ether, 3,4,4'-trichlorobanilide, phenoxyethanol, phenoxy propanol, phenoxyisopropanol, doxycycline, capreomycin, chlorhexidine, chlortetracycline, oxytetracycline, clindamycin, ethambutol, hexamidine isethionate, metronidazole, pentamidine, gentamicin, kanamycin, lineomycin, methacycline, methenamine, minocycline, neomycin, netilmicin, paromomycin, streptomycin, tobramycin, miconazole, tetracycline hydrochloride, erythromycin, zinc erythromycin, erythromycin estolate, erythromycin stearate, amikacin sulfate, doxycycline hydrochloride, capreomycin sulfate, chlorhexidine gluconate, chlorhexidine hydrochloride, chlortetracycline hydrochloride, oxytetracycline hydrochloride, clindamycin hydrochloride, ethambutol hydrochloride, metronidazole hydrochloride, pentamidine hydrochloride, gentamicin sulfate, kanamycin sulfate, lineomycin hydrochloride, methacycline hydrochloride, methenamine hippurate, methenamine mandelate, minocycline hydrochloride, neomycin sulfate, netilmicin sulfate, paromomycin sulfate, streptomycin sulfate, tobramycin sulfate, miconazole hydrochloride, ketoconazole, amanfadine hydrochloride, amanfadine sulfate, octopirox, parachlorometa xylenol, nystatin, tolnaftate, zinc pyrithione and clotrimazole.

Examples of compounds useful herein include those selected from benzoyl peroxide, 3-hydroxy benzoic acid, glycolic acid, lactic acid, 4-hydroxy benzoic acid, 2-hydroxybutanoic acid, 2-hydroxypentanoic acid, 2-hydroxyhexanoic acid, cis-retinoic acid, trans-retinoic acid, retinol, phytic acid, N-acetyl-L-cysteine, lipoic acid, azelaic acid, arachidonic acid, benzoylperoxide, tetracycline, ibuprofen, naproxen, hydrocortisone, acetominophen, resorcinol, phenoxyethanol, phenoxypropanol, phenoxyisopropanol, 2,4,4'-trichloro-2'-hydroxy diphenyl ether, 3,4,4'-trichlorocarbanilide, octopirox, lidocaine hydrochloride, clotrimazole, miconazole, ketoconazole, neocycin sulfate, and mixtures thereof.

Sunscreen Compounds

Exposure to ultraviolet light can result in excessive scaling and texture changes of the stratum corneum. Therefore, the compositions of the subject invention may optionally contain a sunscreen compound. As used herein, "sunscreen compound" includes both sunscreen agents and physical sun blocks. Suitable sunscreen compounds may be organic or inorganic.

Inorganic sunscreens useful herein include the following metallic oxides; titanium dioxide having an average primary particle size of from about 15 nm to about 100 nm, zinc oxide having an average primary particle size of from about 15 nm to about 150 nm, zirconium oxide having an average primary particle size of from about 15 nm to about 150 nm, iron oxide having an average primary particle size of from about 15 nm to about 500 nm, and mixtures thereof. When used herein, the inorganic sunscreens can be present in the amount of from about 0.1% to about 20%, or from about 0.5% to about 10%, or from about 1% to about 5%, by weight of the composition.

A wide variety of conventional organic sunscreen compounds are suitable for use herein. Sagarin, et al., at Chapter VIII, pages 189 et seq., of Cosmetics Science and Technology (1972), discloses numerous suitable compounds. Specific suitable sunscreen compounds include, for example: p-aminobenzoic acid, its salts and its derivatives (ethyl, isobutyl, glyceryl esters; p-dimethylaminobenzoic acid); anthranilates (i.e., o-amino-benzoates; methyl, menthyl, phenyl, benzyl, phenylethyl, linalyl, terpinyl, and cyclohexenyl esters); salicylate esters (amyl, phenyl, octyl, benzyl, menthyl, glyceryl, and di-propyleneglycol esters); cinnamic acid derivatives (menthyl and benzyl esters, a-phenyl cinnamonitrile; butyl cinnamoyl pyruvate); dihydroxycinnamic acid derivatives (umbelliferone, methylumbelliferone, methylaceto-umbelliferone); trihydroxy-cinnamic acid derivatives (esculetin, methylesculetin, daphnetin, and the glucosides, esculin and daphnin); hydrocarbons (diphenylbutadiene, stilbene); dibenzalacetone and benzalacetophenone; naphtholsulfonates (sodium salts of 2-naphthol-3,6-disulfonic and of 2-naphthol-6,8-disulfonic acids); di-hydroxynaphthoic acid and its salts; o- and p-hydroxybiphenyldisulfonates; coumarin derivatives (7-hydroxy, 7-methyl, 3-phenyl); diazoles (2-acetyl-3-bromoindazole, phenyl benzoxazole, methyl naphthoxazole, various aryl benzothiazoles); quinine salts (bisulfate, sulfate, chloride, oleate, and tannate); quinoline derivatives (8-hydroxyquinoline salts, 2-phenylquinoline); hydroxy- or methoxy-substituted benzophenones; uric and violuric acids; tannic acid and its derivatives (e.g., hexaethylether); (butyl carbotol) (6-propyl piperonyl) ether; hydroquinone; benzophenones (oxybenzene, sulisobenzone, dioxybenzone, benzoresorcinol, 2,2',4,4'-tetrahydroxybenzophenone, 2,2'-dihydroxy-4,4'-dimethoxybenzophenone, octabenzone; 4-isopropyldibenzoylmethane; butylmethoxydibenzoylmethane; etocrylene; octocrylene; [3-(4'-methylbenzylidene boman-2-one), terephthalylidene dicamphor sulfonic acid and 4-isopropyl-di-benzoylmethane.

Desirable compounds include 2-ethylhexyl-p-methoxycinnamate (commercially available as PARSOL MCX), 4,4'-t-butyl methoxydibenzoyl-methane (commercially available as PARSOL 1789), 2-hydroxy-4-methoxybenzophenone, octyldimethyl-p-aminobenzoic acid, digalloyltrioleate, 2,2-dihydroxy-4-methoxybenzophenone, ethyl-4-(bis(hydroxypropyl))aminobenzoate, 2-ethylhexyl-2-cyano-3,3-diphenylacrylate, 2-ethylhexyl-salicylate, glyceryl-p-aminobenzoate, 3,3,5-tri-methylcyclohexylsalicylate, methylanthranilate, p-dimethyl-aminobenzoic acid or aminobenzoate, 2-ethylhexyl-p-dimethyl-amino-benzoate, 2-phenylbenzimidazole-5-sulfonic acid, 2-(p-dimethylaminophenyl)-5-sulfonicbenzoxazoic acid, octocrylene and mixtures of these compounds.

In some embodiments, the organic sunscreen compounds used in the compositions of the invention are 2-ethylhexyl-p-methoxycinnamate, butylmethoxydibenzoyl-methane, 2-hydroxy-4-methoxybenzo-phenone, 2-phenylbenzimidazole-5-sulfonic acid, octyldimethyl-p-aminobenzoic acid, octocrylene and mixtures thereof.

Useful sunscreen compounds are also described in U.S. Pat. No. 4,937,370 issued to Sabatelli on Jun. 26, 1990, and U.S. Pat. No. 4,999,186 issued to Sabatelli & Spirnak on Mar. 12, 1991. The sun-screening agents disclosed therein have, in a single molecule, two distinct chromophore moieties that exhibit different ultra-violet radiation absorption spectra. One of the chromophore moieties absorbs predominantly in the UVB radiation range and the other absorbs strongly in the UVA radiation range.

Desirable members of this class of sun-screening agents are 4-N,N-(2-ethylhexyl)methyl-aminobenzoic acid ester of 2,4-dihydroxybenzophenone; N,N-di-(2-ethylhexyl)-4-aminobenzoic acid ester with 4-hydroxydibenzoylmethane; 4-N,N-(2-ethylhexyl)methyl-aminobenzoic acid ester with 4-hydroxydibenzoylmethane; 4-N,N-(2-ethylhexyl)methyl-aminobenzoic acid ester of 2-hydroxy-4-(2-hydroxyethoxy) benzophenone; 4-N,N-(2-ethylhexyl)-methylaminobenzoic acid ester of 4-(2-hydroxyethoxy)dibenzoylmethane; N,N-di-(2-ethylhexyl)-4-aminobenzoic acid ester of 2-hydroxy-4-(2-hydroxyethoxy)benzophenone; and N,N-di-(2-ethylhexyl)-4-aminobenzoic acid ester of 4-(2-hydroxyethoxy) dibenzoylmethane and mixtures thereof. Other desirable sunscreen compounds include 4,4'-t-butylmethoxydibenzoyl-methane, 2-ethylhexyl-p-methoxycinnamate, phenyl benzimidazole sulfonic acid, and octocrylene.

A safe and effective amount of the organic sunscreen compound is used, typically from about 1% to about 20%, more typically from about 2% to about 10% by weight of the composition. Exact amounts will vary depending upon the sunscreen or sunscreens chosen and the desired Sun Protection Factor (SPF).

Particulate Material

The compositions of the invention may contain a particulate material, for example, a metallic oxide. These particulates can be coated or uncoated, charged or uncharged. Charged particulate materials are disclosed in U.S. Pat. No. 5,997,887, to Ha, et al., incorporated herein by reference. Particulate materials useful herein include; bismuth oxychloride, iron oxide, mica, mica treated with barium sulfate and $TiO_2$, silica, nylon, polyethylene, talc, styrene, polypropylene, ethylene/acrylic acid copolymer, sericite, titanium dioxide, bismuth oxychloride, iron oxide, aluminum oxide, silicone resin, barium sulfate, calcium carbonate, cellulose acetate, polymethyl methacrylate, and mixtures thereof.

Inorganic particulate materials, e.g., $TiO_2$, $ZnO$, or $ZrO_2$ are commercially available from a number of sources. One example of a suitable particulate material contains the material available from U.S. Cosmetics (TRONOX $TiO_2$ series, SAT-T CR837, a rutile $TiO_2$). Particulate materials can be present in the composition in levels of from about 0.01% to about 2%, or from about 0.05% to about 1.5%, or from about 0.1% to about 1%, by weight of the composition.

Conditioning Agents

The compositions of the present invention may contain a conditioning agent selected from humectants, moisturizers, or skin conditioners. A variety of these materials can be employed and each can be present at a level of from about 0.01% to about 20%, more preferably from about 0.1% to about 10%, and still more preferably from about 0.5% to about 7% by weight of the composition. These materials include, but are not limited to, guanidine; urea; glycolic acid and glycolate salts (e.g. ammonium and quaternary alkyl ammonium); lactic acid and lactate salts (e.g., ammonium and quaternary alkyl ammonium); aloe vera in any of its variety of forms (e.g., aloe vera gel); polyhydroxy alcohols such as sorbitol, mannitol, xylitol, erythritol, glycerol, hexanetriol, butanetriol, propylene glycol, butylene glycol, hexylene glycol and the like; polyethylene glycols; sugars (e.g., melibiose) and starches; sugar and starch derivatives (e.g., alkoxylated glucose, fucose, glucosamine); hyaluronic acid; lactamide monoethanolamine; acetamide monoethanolamine; panthenol; allantoin; and mixtures thereof. Also useful herein are the propoxylated glycerols described in U.S. Pat. No. 4,976,953, to Orr et al, issued Dec. 11, 1990.

Also useful are various $C_1$–$C_{30}$ monoesters and polyesters of sugars and related materials. These esters are derived from a sugar or polyol moiety and one or more carboxylic acid moieties. Such ester materials are further described in, U.S. Pat. No. 2,831,854; U.S. Pat. No. 4,005,196, to Jandacek, issued Jan. 25, 1977; U.S. Pat. No. 4,005,195, to Jandacek, issued Jan. 25, 1977; U.S. Pat. No. 5,306,516, to Letton et al, issued Apr. 26, 1994; U.S. Pat. No. 5,306,515, to Letton et al, issued Apr. 26, 1994; U.S. Pat. No. 5,305,514, to Letton et al, issued Apr. 26, 1994; U.S. Pat. No. 4,797,300, to Jandacek et al, issued Jan. 10, 1989; U.S. Pat. No. 3,963,699, to Rizzi et al, issued Jun. 15, 1976; U.S. Pat. No. 4,518,772, to Volpenhein, issued May 21, 1985; and U.S. Pat. No. 4,517,360, to Volpenhein, issued May 21, 1985.

Desirable conditioning agents are selected from urea, guanidine, sucrose polyester, panthenol, dexpanthenol, allantoin, and combinations thereof.

Thickening Agent

The compositions of the present invention can contain one or more thickening agents, can be from about 0.1% to about 5%, or from about 0.1% to about 4%, or from about 0.25% to about 3%, by weight of the composition. Nonlimiting classes of thickening agents include those selected from the following:

a) Carboxylic Acid Polymers

These polymers are crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol. Polymers useful in the present invention are more fully described in U.S. Pat. No. 5,087,445, to Haffey et al, issued Feb. 11, 1992; U.S. Pat. No. 4,509,949, to Huang et al, issued Apr. 5, 1985; U.S. Pat. No. 2,798,053, to Brown, issued Jul. 2, 1957; and in CTFA International Cosmetic Ingredient Dictionary, Fourth Edition, 1991, pp. 12 and 80.

Examples of commercially available carboxylic acid polymers useful herein include the carbomers, which are homopolymers of acrylic acid crosslinked with allyl ethers of sucrose or pentaerytritol. The carbomers are available as the Carbopol™ 900 series from B.F. Goodrich (e.g., Carbopol™ 954). In addition, other suitable carboxylic acid polymeric agents include copolymers of $C_{10-30}$ alkyl acrylates with one or more monomers of acrylic acid, methacrylic acid, or one of their short chain (i.e., $C_{1-4}$ alcohol) esters, wherein the crosslinking agent is an allyl ether of sucrose or pentaerytritol. These copolymers are known as acrylates/$C_{10-30}$ alkyl acrylate crosspolymers and are commercially available as Carbopol™ 1342, Carbopol™ 1382, Pemulen TR-1, and Pemulen TR-2, from B.F. Goodrich. In other words, examples of carboxylic acid polymer thickeners useful herein are those selected from carbomers, acrylates/$C_{10}$-$C_{30}$ alkyl acrylate crosspolymers, and mixtures thereof.

b) Crosslinked Polyacrylate Polymers

The compositions of the present invention can optionally contain crosslinked polyacrylate polymers useful as thickeners or gelling agents including both cationic and nonionic polymers, with the cationics being generally preferred. Examples of useful crosslinked nonionic polyacrylate polymers and crosslinked cationic polyacrylate polymers are those described in U.S. Pat. No. 5,100,660, to Hawe et al, issued Mar. 31, 1992; U.S. Pat. No. 4,849,484, to Heard, issued Jul. 18, 1989; U.S. Pat. No. 4,835,206, to Farrar et al, issued May 30, 1989; U.S. Pat. No. 4,628,078 to Glover et al issued Dec. 9, 1986; U.S. Pat. No. 4,599,379 to Flesher et al issued Jul. 8, 1986; and EP 228,868, to Farrar et al, published Jul. 15, 1987.

c) Polyacrylamide Polymers

The compositions of the present invention can optionally contain polyacrylamide polymers, especially nonionic polyacrylamide polymers including substituted branched or unbranched polymers. More preferred among these polyacrylamide polymers is the nonionic polymer given the CTFA designation polyacrylamide and isoparaffin and laureth-7, available under the Trade name Sepigel 305 from Seppic Corporation (Fairfield, N.J.).

Other polyacrylamide polymers useful herein include multi-block copolymers of acrylamides and substituted acrylamides with acrylic acids and substituted acrylic acids. Commercially available examples of these multi-block copolymers include Hypan SR150H, SS500V, SS500W, SSSA100H, from Lipo Chemicals, Inc., (Patterson, N.J.).

d) Polysaccharides

A wide variety of polysaccharides are useful herein. "Polysaccharides" refer to gelling agents that contain a backbone of repeating sugar (i.e., carbohydrate) units. Nonlimiting examples of polysaccharide gelling agents include those selected from cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Also useful herein are the alkyl-substituted celluloses. In these polymers, the hydroxy groups of the cellulose polymer is hydroxyalkylated (preferably hydroxyethylated or hydroxypropylated) to form a hydroxyalkylated cellulose that is then further modified with a $C_{10}$–$C_{30}$ straight chain or branched chain alkyl group through an ether linkage. Typically these polymers are ethers of $C_{10}$–$C_{30}$ straight or branched chain alcohols with hydroxyalkylcelluloses. Examples of alkyl groups useful herein include those selected from stearyl, isostearyl, lauryl, myristyl, cetyl, isocetyl, cocoyl (i.e. alkyl groups derived from the alcohols of coconut oil), palmityl, oleyl, linoleyl, linolenyl, ricinoleyl, behenyl, and mixtures thereof. Preferred among the alkyl hydroxyalkyl cellulose ethers is the material given the CTFA designation cetyl hydroxyethylcellulose, which is the ether of cetyl alcohol and hydroxyethylcellulose. This material is sold under the trade name Natrosol™ CS Plus from Aqualon Corporation (Wilmington, Del.).

Other useful polysaccharides include scleroglucans that are a linear chain of (1–3) linked glucose units with a (1–6) linked glucose every three units, a commercially available example of which is Clearogel™ CS11 from Michel Mercier Products Inc. (Mountainside, N.J.).

e) Gums

Other thickening and gelling agents useful herein include materials that are primarily derived from natural sources. Nonlimiting examples of these gelling agent gums include acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluroinic acid, hydrated silica, hydroxypropyl chitosan, hydroxypropyl guar, karaya gum, kelp, locust bean gum, natto gum, potassium alginate, potassium carrageenan, propylene glycol alginate, sclerotium gum, sodium carboyxmethyl dextran, sodium carrageenan, tragacanth gum, xanthan gum, and mixtures thereof.

Compositions of the invention can therefore include desirable thickening agents such as carboxylic acid polymers, crosslinked polyacrylate polymers, polyacrylamide polymers, and mixtures thereof, more preferably selected from carboxylic acid polymers, polyacrylamide polymers, and mixtures thereof.

Composition Preparation

The compositions useful for the methods of the present invention are generally prepared by conventional methods such as are known in the art of making topical compositions. Such methods typically involve mixing of the ingredients in one or more steps to a relatively uniform state, with or without heating, cooling, application of vacuum, and the like.

Articles Containing Cyclic Peptide Inhibitors

The peptides of the present invention may be delivered to the skin from absorbent articles. As used herein, the term "absorbent article" refers to a device with absorbs and retains body exudates. Examples of absorbent articles include feminine hygiene garments, sanitary napkins, panty liners, tampons, diapers, incontinence briefs, diaper holders, training pants, and the like.

In some embodiments, the peptides of the present invention are delivered from an absorbent article such as a diaper. As used herein, the term "diaper" refers to an absorbent article generally worn by infants and incontinent persons that is worn about the lower torso of the wearer. In other words, the term "diaper" includes infant diapers, training pants, incontinence briefs, and the like.

The peptides may be incorporated into the absorbent articles neat, such as in dry powder or particulate form, or incorporated into, for example, an aqueous-based pharmaceutically and dermatologically acceptable composition. By "aqueous" is meant any hydrophilic vehicle including, but not limited to, those containing water, alcohols, polymeric hydrogels, weak bases, metal salts, and/or the like that do not interfere, to any significant degree, with the enzyme inhibitory activity of the peptide. The peptides may also be incorporated into a water-in-oil emulsion, into hydrophobic compositions and/or as the aqueous components of oil-in-water emulsions. The composition may or may not be pH buffered and, although the initial pH of the peptide/composition may range from about 3.5 to about 9.5, depending on its intended location in the absorbent article, it is desirable that the peptide/composition intended for direct contact with the skin have an initial pH no less than 3.5 and no greater than about 7.5, and preferably from about 6.8 to about 7.4.

The compositions of the present invention comprise a safe and effective amount of a peptide of the present invention whether delivered as a composition (e.g. a lotion) or from an absorbent article. When compositions are delivered from an absorbent article, the compositions can comprise from about 0.01% to about 20%, or from about 1.0% to about 10%, or from about 10%, by weight, of a peptide of the present invention.

The present invention also provides a composition having one or more of the cyclic peptides of the invention joined to a substrate. This substrate-associated composition can be employed in absorbent articles such as those described above. The cyclic peptides can be slowly released from the substrate, for example, when the substrate is exposed to bodily fluids or wastes (e.g. urine, feces, blood, menstrual fluid, vaginal exudate, urine and perspiration). The cyclic peptides present on or within the articles of the invention can inhibit the activity of proteases in such bodily fluids or wastes and thereby protect the skin from irritations and rashes.

Therefore, one embodiment of the present invention provides a composition having one or more of the cyclic peptides of the invention wherein the composition is joined or adsorbed to a substrate. In some embodiments, the cyclic peptides of the invention are joined to a substrate by absorption into the substrate; in other embodiments, the cyclic peptides of the invention are joined to a substrate by covalent linkage to functional groups in the substrate. Side chain moieties on the amino acids that comprise the peptides of the invention can be used for such covalent linkage.

In another embodiment, the invention provides a composite two-layer article comprising a composition of one or more cyclic peptides wherein the composition is joined or adsorbed onto a first layer of the article and a second layer that can be absorbent. A third water-proof layer can also be utilized in the articles of the invention. In normal use, it is understood that the inner side or inner layer of the article will typically be exposed to the bodily fluids or wastes. The term "inner layer" or "inner side," as used herein, means the layer or side of the article closest to the skin of the wearer. The composition of the invention can be absorbed, adsorbed or linked to the first layer. Such a first layer can be in direct contact with the skin or, alternatively, the first layer with the composition can be positioned within the article so that the composition is not in direct contact with the skin. In the later case, a thin liner may be used that permits passage of fluids and some particles into the body of the article. The second absorbent layer can facilitate absorption and transport body fluids and wastes from the skin into the diaper material, effectively removing those fluids and wastes and further exposing the fluids and wastes to the composition.

The composition can be applied to the article at any point during assembly. For example, the composition can be applied to the finished disposable absorbent product before it has been packaged. The composition can also be applied to a given component (e.g., topsheet, liner, absorbent layer, cuffs, sides, waist, etc.), at the manufacturing site or by the material supplier, before it is combined with the other raw materials to form a finished disposable absorbent product. The composition can be applied to other zones of the article such that the composition will migrate to one or more wearer contacting surfaces during use.

The peptides of the present invention, or the compositions comprising them, may also be incorporated into absorbent articles in any delivery system known to those skilled in the art that facilitates contact of an enzyme inhibitor with fecal, blood or other matter to inhibit enzyme activity therein and/or that facilitates the transfer of a peptide or composition to the skin of the wearer of the article to protect against irritation due to enzymes at the skin interface. The delivery system may be a component of any portion or portions of the absorbent article. Such delivery systems include those which deliver the compound neat and those in which the compound is delivered from a vehicle (composition). See, e.g., U.S. Pat. No. 6,066,673.

Methods for Regulating Skin Condition

The compositions of the present invention are useful for protecting the skin by inhibiting protease activity and promoting healthy skin development. The compositions of the invention can be used for both prophylactic and therapeutic treatment of skin conditions. For example, compositions of the invention can be used for preventing skin irritations, preventing rashes, promoting healing of skin tissue after a rash or irritation has occurred (i.e., building the epidermis and/or dermis layers of the skin), preventing and/or retarding atrophy of mammalian skin, preventing and/or retarding the appearance of spider vessels and/or red blotchiness on mammalian skin, preventing and/or relieving itching in mammalian skin, regulating skin texture (e.g. ameliorating roughness, swelling and soreness), and improving skin color (e.g. redness).

Treating skin tissues involves topically applying to the skin tissue a safe and effective amount of a composition of the present invention. The amount of the composition that is applied, the frequency of application and the period of use will vary widely depending upon the amount of the active peptide and other ingredients in a given composition and the level of regulation desired, for example, in light of the level of skin tissue damage present or expected to occur.

In some embodiments, the composition is chronically applied to the skin. By "chronic topical application" is meant continued topical application of the composition over an extended period during the subject's lifetime, for example, for a period of at least about one week, or for a period of at least about one month, or for at least about three months, or for at least about six months, or for at least about one year. While benefits are obtainable after various periods of use (e.g., two, five, ten or twenty days), chronic application can continue for a year or more. Typically applications would be on the order of about once per day over such extended periods, however application rates can vary from about once per week up to about three times per day or more.

A wide range of quantities of the compositions of the present invention can be employed to provide a beneficial effect upon the skin. Quantities of the present compositions that are typically applied per application are, in mg composition/$cm^2$ skin, from about 0.01 mg/$cm^2$ to about 10 mg/$cm^2$. A desirable and useful application amount is about 1 mg/$cm^2$ to about 2 mg/$cm^2$.

Regulating skin tissue condition can be practiced by applying a composition in the form of a skin lotion, cream, gel, foam, ointment, paste, emulsion, spray, conditioner, tonic, or the like that is preferably intended to be left on the skin or other keratin structure for some esthetic, prophylactic, therapeutic or other benefit (i.e., a "leave-on" composition). After applying the composition to the skin, it can be left on the skin for a period of at least about 15 minutes, or at least about 30 minutes, or at least about 1 hour, or for at least several hours or, for example, at least about 12 hours.

Any part of the external portion of the skin including the diaper or genital area, the torso, arms, hands, legs, feet, scalp, etc. The composition can be applied with the fingers, with an implement or device, or in personal care items such as diapers, tampons, feminine care pads, cotton balls, spray applicators, and the like.

Another approach to ensure a continuous exposure of the skin to at least a minimum level of the beneficial compositions of the invention is to apply the composition in a diaper, feminine care pad or patch, for example, to selected tissues such as the diaper area or the genitals. A patch may be particularly useful for problem skin areas needing more intensive treatment (e.g., a wound, an ongoing irritation or rash and the like).

EXAMPLE 1

Fecal Protease Inhibition Assay

By way of illustration, the cyclic peptides of the present invention may be tested in a standard enzyme assay for protease activity to determine their activity for inhibiting fecal and other proteases.

Infant feces are collected in a manner to keep them free from urine contamination and mixed with water to obtain a weight by weight (w/w) mixture (e.g., 1:4 w/w). This mixture is then mixed thoroughly to obtain a homogeneous suspension by homogenization or sonication. The feces are then diluted with a reaction buffer, described below, to obtain a fecal concentration that, when added to a protease substrate, hydrolyzes the substrate over a 5 to 60 minute period. Using such a method, for example, fecal trypsin activity may be determined at pH 8.2 in a 50 nM Tris-HCl buffer with 20 mM $CaCl_2$, containing 0.3 mM of the composition to be tested; fecal chymotrypsin activity at pH 7.6 in a 50 mM Tris-HCl buffer with 20 mM $CaCl_2$, containing 0.05 mM of the composition to be tested; and fecal leucine aminopeptidase activity at pH 7.2 in 50 mM sodium phosphate containing the composition to be tested. To test the efficacy of the compositions, several different concentrations of each cyclic peptide are added to duplicate feces-containing reaction buffers, and the inhibition of the enzyme activity is measured. Peptides having an $IC_{50}$ of 100 µM or less are desirable peptides of the invention. Other desirable peptides of the invention have an $IC_{50}$ to $IC_{90}$, or an $IC_{80}$ to $IC_{90}$, of 100 µM or less.

All patents and publications referenced or mentioned herein are indicative of the levels of skill of those skilled in the art to which the invention pertains, and each such referenced patent or publication is hereby incorporated by reference to the same extent as if it had been incorporated by reference in its entirety individually or set forth herein in its entirety. Applicants reserve the right to physically incorporate into this specification any and all materials and information from any such cited patents or publications.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. The methods and processes illustratively described herein suitably may be practiced in differing orders of steps, and that they are not necessarily restricted to the orders of steps indicated herein or in the claims. As used herein and in the appended claims, the singular forms "a," "an," and "the" include plural reference unless the context clearly dictates otherwise. Thus, for example, a reference to "a host cell" includes a plurality (for example, a culture or population) of such host cells, and so forth. Under no circumstances may the patent be interpreted to be limited to the specific examples or embodiments or methods specifically disclosed herein. Under no circumstances may the patent language be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

What is claimed:

1. A method for treating a skin irritation on a mammal comprising topically administering to the mammal an effective amount of one or more cyclic peptides that consist of SEQ ID NO:1 (CTKSIPPIC), SEQ ID NO:2 (GRCTKSIP-PICFPD) or SEQ ID NO:3 (IPPICFPDGRCTK).

2. The method of claim 1, wherein more than one of the peptides is administered.

3. The method of claim 1, wherein the skin irritation is primarily caused by proteolytic enzymes that are present in human feces, menstrual fluids, nasal fluids, colostomy fluids, dandruff or healing wounds.

4. The method of claim 1, wherein one or more of the cyclic peptides is bound by a serine protease but is not cleaved by the serine protease.

5. The method of claim 1, wherein one or more of the cyclic peptides inhibits serine protease activity.

6. The method of claim 1, wherein one or more of the cyclic peptides inhibits protease activity of trypsin, β-trypsin, chymotrypsin, cathepsin G, aminopeptidase, elastase, matripase or thrombin.

7. The method of claim 1, wherein one or more of the cyclic peptides is administered from an absorbent article.

8. The method of claim 1, wherein the method further comprises administering hyaluronic acid.

* * * * *